US006224556B1

(12) United States Patent
Schwartz et al.

(10) Patent No.: US 6,224,556 B1
(45) Date of Patent: May 1, 2001

(54) DIAGNOSTIC MEDICAL ULTRASOUND SYSTEM AND METHOD FOR USING A SPARSE ARRAY

(75) Inventors: Jodi L. Schwartz, Sunnyvale; John I. Jackson, Menlo Park; Jay S. Plugge, Sunnyvale, all of CA (US)

(73) Assignee: Acuson Corporation, Mountain View, CA (US)

( * ) Notice: Subject to any disclaimer, the term of this patent is extended or adjusted under 35 U.S.C. 154(b) by 0 days.

(21) Appl. No.: 09/200,649

(22) Filed: Nov. 25, 1998

(51) Int. Cl.[7] .................................................. A61B 8/00
(52) U.S. Cl. ............................................................ 600/447
(58) Field of Search .................................. 600/443, 447, 600/448, 449, 437

(56) References Cited

U.S. PATENT DOCUMENTS

| | | |
|---|---|---|
| 3,938,502 | 2/1976 | Bom . |
| 4,917,097 | 4/1990 | Proudian et al. . |
| 5,285,788 | 2/1994 | Arenson et al. . |
| 5,297,553 | 3/1994 | Sliwa, Jr. et al. . |
| 5,345,940 | 9/1994 | Seward et al. . |
| 5,456,257 | 10/1995 | Johnson et al. . |
| 5,549,111 | 8/1996 | Wright et al. . |
| 5,551,433 | 9/1996 | Wright et al. . |
| 5,555,534 | 9/1996 | Maslak et al. . |
| 5,570,691 | 11/1996 | Wright et al. . |
| 5,577,505 | 11/1996 | Brock-Fisher et al. . |
| 5,581,517 | 12/1996 | Gee et al. . |
| 5,617,862 | 4/1997 | Cole et al. . |
| 5,623,928 | 4/1997 | Wright et al. . |
| 5,632,277 | 5/1997 | Chapman et al. . |

(List continued on next page.)

FOREIGN PATENT DOCUMENTS 0 770 352 A1   5/1997  (EP) .

OTHER PUBLICATIONS

Richard E. Kerber, MD, Coronary Risk Areas: Measurements by Intracardiac Echo and Ultrasound Contrast, Sep., 1998, p. 8.

James B. Seward et al, *Mayo Clinic Proceedings Ultrasound Cardioscopy: Embarking on a New Journey*, Jul., 1996, vol. 71, No. 7, pp. 629–635.

Primary Examiner—Marvin M. Lateef
Assistant Examiner—Maolin Patel
(74) Attorney, Agent, or Firm—Craig A. Summerfield, Esq.; Brinks Hofer Gilson & Lione

(57) ABSTRACT

A method and system for obtaining ultrasound data with a sparse array of transducer elements is provided. About one wavelength of a highest operating frequency separates the center of each transducer element from any adjacent transducer element. While this spacing may generate grating lobes, the beamformer of the ultrasound system is configured to filter and isolate information at a harmonic of a fundamental transmit frequency. The resultant two-way beam pattern is less effected by the grating lobes. The image generated as a function of the harmonic information has few artifacts created as a function of the sparse spacing of the transducer elements. Given a set number of beamformer transmit channels, the sparse spacing may allow for a larger aperture width with few artifacts as a result of sparse element spacing. The larger aperture width generates a narrower beam in the azimuthal dimension of a one-dimensional transducer. By generating a narrower beam, better azimuthal resolution may be obtained. Alternatively, the number of transmit channels may be reduced to provide a beam width that is the same or similar to a beam generated with a conventional phased array where transducer elements have a one-half of the wavelength spacing of the fundamental frequency. By using fewer transmit channels to obtain the same beam width, the space required by electrical traces connecting the transducer elements to the beamformer is reduced. The reduced required space is beneficially used on catheter or intravascular transducers.

45 Claims, 3 Drawing Sheets

U.S. PATENT DOCUMENTS

| | | |
|---|---|---|
| 5,667,373 | 9/1997 | Wright et al. . |
| 5,699,805 | 12/1997 | Seward et al. . |
| 5,713,363 | 2/1998 | Seward et al. . |
| 5,740,808 | 4/1998 | Panescu et al. . |
| 5,793,701 | 8/1998 | Wright et al. . |
| 5,795,299 | 8/1998 | Eaton et al. . |
| 5,797,848 | 8/1998 | Marian et al. . |
| 5,808,962 | 9/1998 | Steinberg et al. . |
| 5,823,962 | 10/1998 | Schaetzle et al. . |
| 5,833,613 | 11/1998 | Averkiou et al. . |
| 5,846,205 | 12/1998 | Curley et al. . |
| 5,902,241 * | 5/1999 | Seyed-Bolorfrosh ................ 600/443 |
| 5,938,612 * | 8/1999 | Kline-Schoder et al. ........... 600/459 |
| 6,014,897 * | 1/2000 | Mo ........................................ 73/628 |
| 6,077,226 * | 6/2000 | Washburn et al. ................... 600/443 |

\* cited by examiner

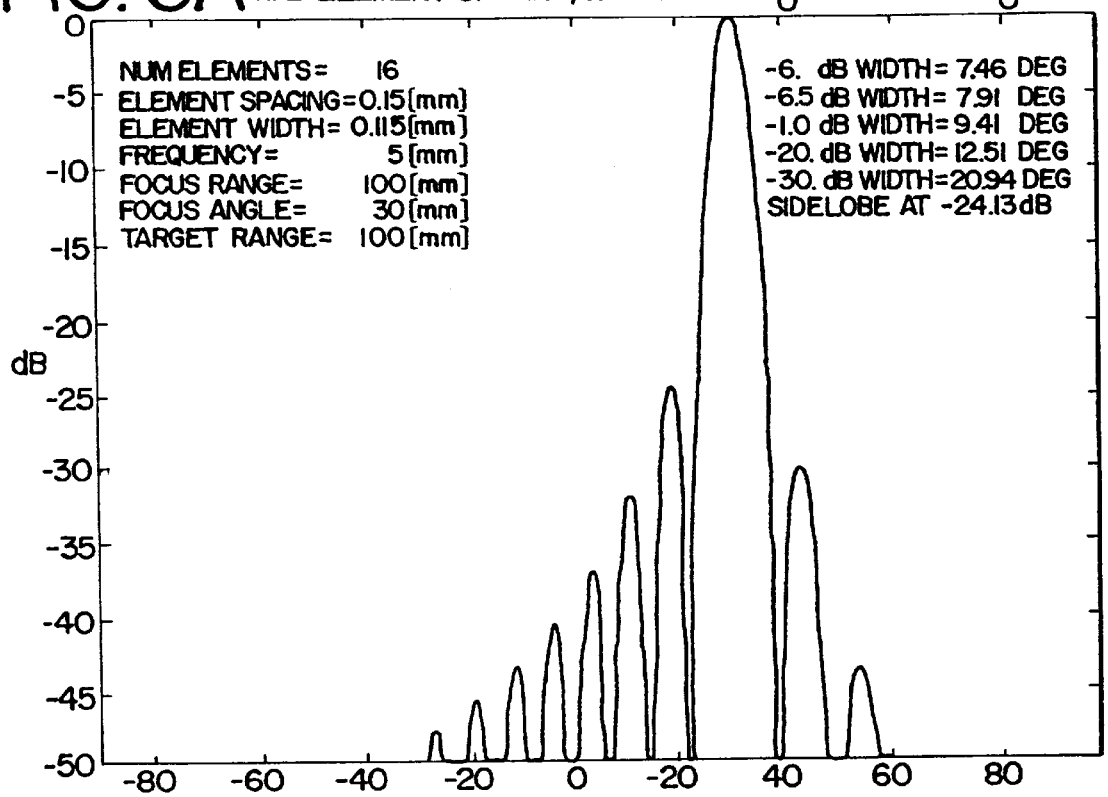
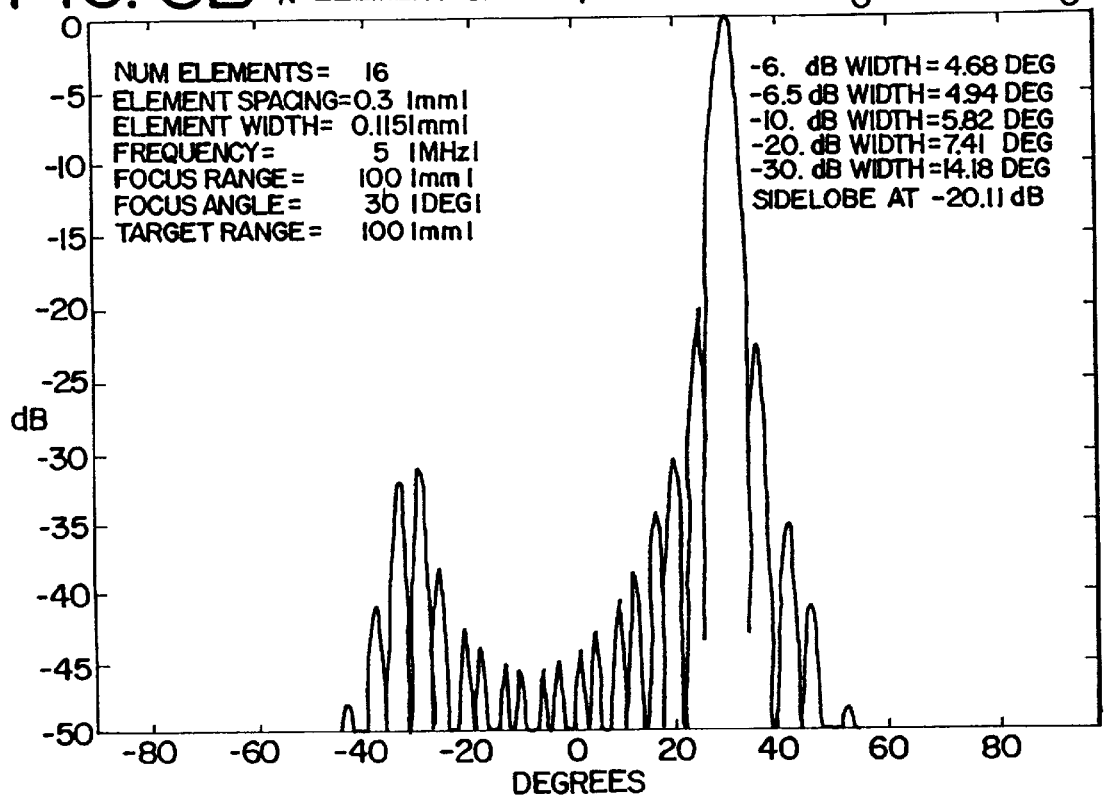

DIAGNOSTIC MEDICAL ULTRASOUND SYSTEM AND METHOD FOR USING A SPARSE ARRAY

BACKGROUND OF THE INVENTION

This invention relates to an ultrasound system and method for obtaining ultrasound data with an array of transducer elements. In particular, the transducer elements are spaced to create a sparse ultrasonic phased array.

Ultrasound systems include a beamformer and an image processor. The beamformer generates transmit waveforms and coherently sums reflected receive signals. The beamformer also filters the information. The filtering may be selectable between a harmonic and a fundamental frequency. For example, the filter isolates information associated with a second harmonic frequency of a fundamental transmit frequency. The coherently summed information is processed by the image processor to generate an image on a display.

The transmit waveforms from the beamformer are converted to acoustical energy, and the reflected acoustical energy is converted into receive signals by an array of transducer elements. In order to avoid grating lobes in steered transducer arrays, the distance from the center of a transducer element to the center of adjacent transducer elements is maintained at around one-half a wavelength of a transmit and receive center frequency. In non-steered arrays, this distance is on the order of one wavelength. Increasing the lateral resolution by using a larger transducer extent in the lateral dimension would require a greater number of transducer elements. However, increasing the number of elements increases the cost and complexity of the transducer and the associated beamformer. For example, the number of beamformer transmit and receive channels is increased.

BRIEF SUMMARY

The present invention is defined by the following claims, and nothing in this section should be taken as a limitation on those claims. By way of introduction, the preferred embodiment described below includes a method and system for obtaining ultrasound data with a sparse array of transducer elements. The transducer elements are spaced. About one to two wavelengths of a highest operating frequency (i.e., the transmit fundamental or the harmonic receive frequency) separates the center of each transducer element from the center of any adjacent transducer element for a steered array. For a non-steered array, the separation is about two to four wavelengths of the highest operating frequency, such as a second harmonic receive frequency. While this spacing may generate grating lobes, the beamformer of the ultrasound system is configured to transmit at a fundamental frequency and to filter and isolate receive information at a harmonic of the fundamental transmit frequency. The resulting two-way beam pattern is effected less by the grating lobes. The image generated as a function of the harmonic information has little or no artifacts created as a function of the sparse spacing of the transducer elements.

Given a set number of beamformer transmit channels, the sparse spacing may allow for a larger aperture. A larger aperture generates a narrower beam in the azimuthal dimension of a one-dimensional transducer. By generating a narrower beam, better azimuthal resolution is obtained. Alternatively, the number of transmit channels may be reduced by one-half to provide a beam width that is the same or similar to a beam generated with transducer elements having a one-half wavelength spacing of the highest operating frequency for a steered array. By using fewer transmit channels to obtain the same beam width, the space required by the number of individual electrical traces connecting each transducer element to the beamformer is reduced. The reduced required space is beneficially used in catheter or intravascular transducers.

In one aspect of the embodiments described below, acoustic energy is generated at a fundamental frequency. Using a steered array of transducer elements that are spaced by at least about one wavelength of a highest operating frequency, such as a second harmonic of the fundamental transmit frequency, information is obtained at a harmonic of the fundamental transmit frequency from reflected acoustic energy. In another aspect, a non-steered array has transducer elements that are spaced by at least about two wavelengths of the highest operating frequency.

Further aspects and advantages of the invention are discussed below in conjunction with the preferred embodiments.

BRIEF DESCRIPTION OF SEVERAL VIEWS OF THE DRAWINGS

FIGS. 5A and 5B are graphical representations of beam plots demonstrating the effects of element spacing with fundamental and harmonic receive processing, respectively.

DETAILED DESCRIPTION OF THE INVENTION

In the preferred embodiments described below, a sparse ultrasonic phased array is used to transmit and receive acoustic energy. For example, the center of at least one transducer element is spaced from the center of an adjacent transducer element by at least about one wavelength of a highest operating frequency, such as a second harmonic of the transmit center frequency, in a steered array. In one embodiment, the spacing is double a conventional transducer spacing, such as one to 1.9 or two to 3.8 wavelengths of a second harmonic of a fundamental transmit frequency for steered or non-steered transducer arrays, respectively. For other higher harmonics, N, of the fundamental transmit frequency, the spacing is N times the wavelength of the fundamental frequency for steered and 2N for non-steered transducer arrays. In the case of sub harmonics, the sparse array beam spacing is based on the fundamental transmit frequency rather than the sub harmonic frequency. For example, for a 1/N sub harmonic frequency, the sparse spacing may be 2 to 3 wavelengths of the fundamental frequency with a non-steered array. The artifacts generated from the grating lobes due to the sparse ultrasonic phased array are reduced by imaging with harmonic information. Harmonic imaging with the sparse array may allow for a more narrow beam and resulting better resolution or the same resolution using fewer channels.

Figure 1:
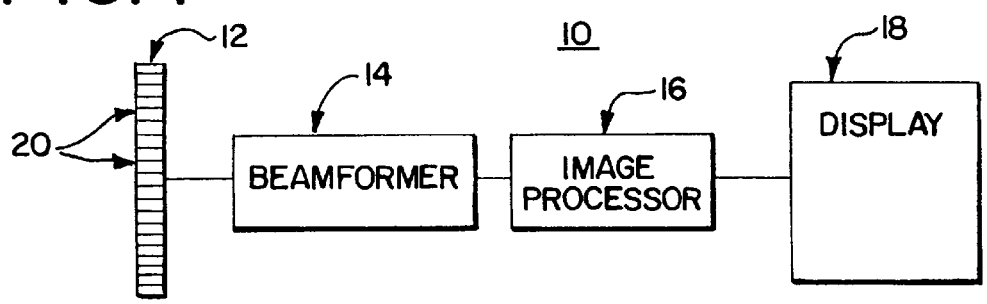
FIG. 1 is a block diagram of an ultrasound system for obtaining ultrasound data at a harmonic of a fundamental transmit frequency.

Referring to FIG. 1, an ultrasound system for harmonic imaging with a sparse array 12 is generally shown at 10. The ultrasound system includes the sparse transducer array 12, a beamformer 14, an image processor 16, and a display 18. The various elements of FIG. 1 may be formed in any suitable manner, including a wide variety of conventional systems. The widest variety of beamformers, image processors and displays may be adapted for use with this invention. Both analog and digital beamformer systems are suitable. By way of example, without intending any limitation, any one of the ultrasound imaging systems marketed by Acuson Corporation under the tradenames 128XP®, Aspen™, and Sequoia® are capable of being modified to implement this invention. Other systems, such as from other manufacturers, may be used.

The beamformer 14 comprises a programmable transmit/receive beamformer for generating transmit waveforms at a fundamental frequency and isolating received reflection information at a harmonic of the fundamental frequency. As used herein, harmonic is intended broadly to include sub-harmonics and fractional harmonic energy (e.g., N=one-half or three-halves of the fundamental frequency at which the transmit beam is centered), as well as higher harmonics (e.g., N=two or three times the fundamental frequency at which the transmit beam is centered).

To obtain the harmonic information, a filter is provided. The filter is preferably a programmable band pass filter. The filter passes the desired harmonic frequency and filters out the fundamental frequency and other undesired harmonic frequencies. In alternative embodiments, the filter demodulates the coherently summed signals to a base band frequency. Signals associated with frequencies other than near the base band are removed or reduced by low pass filtering. Non-programmable, digital or analog beamformers may be used.

The sparse transducer array 12 connected to the beamformer 14 includes an array of transducer elements 20, such as 256, 128, 64 or another number of transducer elements 20. The sparse transducer array 12 is a one dimensional, 1.5 dimensional or two dimensional array. For example, the sparse transducer array 12 comprises a steered or non-steered linear array, a steered or non-steered curved array, a Vector® array, a sector array, or a curved Vector® array. As used herein, a steered array comprises arrays designed for transmitting along ultrasound lines that are not perpendicular to a source element in the active aperture (i.e., the element intersected by the scan line). For example, relative delays are used to steer the scan line, such as steering up to 45 degrees with a sector transducer array. A non-steered array comprises arrays for transmitting only along scan lines that are substantially perpendicular to the source element, such as a linear or curved linear array. Some moderate steering may be performed using a non-steered array, such as up to 25 degrees from perpendicular for Color Doppler imaging.

Figure 3:
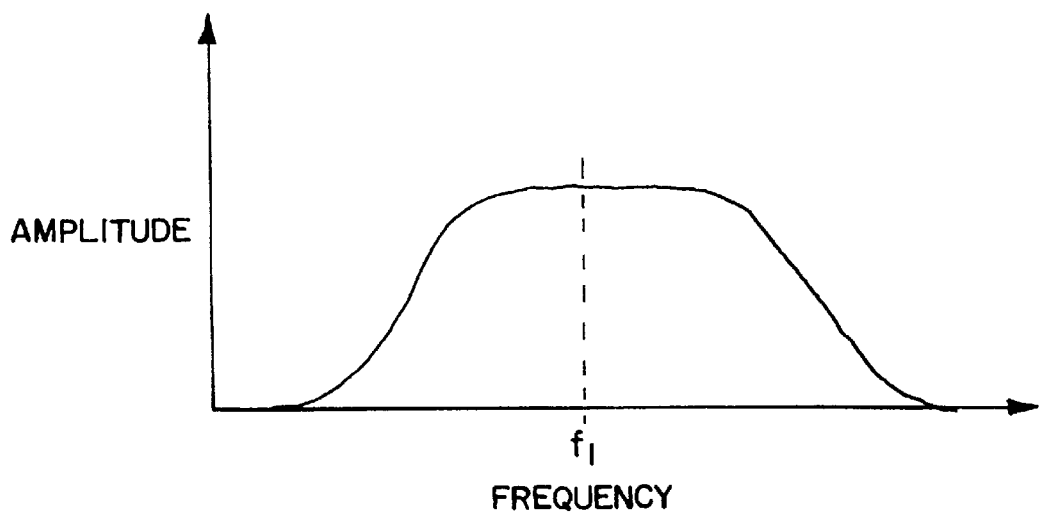
FIG. 3 is a frequency spectrum representing the frequency bandwidth of a transducer.

The sparse transducer array 12 acts as a band pass filter and corresponds to an associated bandwidth, as shown in FIG. 3. Preferably, the bandwidth is wide enough to allow transmission of fundamental frequency signals and reception of the desired Nth harmonic information. For example, the bandwidth allows transmission at 2.5 MHz and reception at the second harmonic 5 MHz.

At least a majority of adjacent transducer elements 20 of a steered array are spaced by about one to two wavelengths of the highest operating frequency, such as a second harmonic of the fundamental transmit frequency. As used herein, the "highest operating" frequency includes the highest of the transmit or receive frequency. For example, a second harmonic receive frequency of a fundamental transmit frequency is the highest operating frequency, and a fundamental transmit frequency is the highest operating frequency where a sub-harmonic receive frequency is used. In one embodiment, all of the transducer elements 20 are associated with a one or 1.5 wavelength spacing from adjacent transducer elements. For non-steered arrays, the spacing is about two to four wavelengths of the highest operating frequency. For example, a spacing of about three wavelengths is used.

The spacing is measured from the center of a transducer element 20 to the center of another transducer element 20. For transducer elements with an irregular shape, the center may be determined as a function of the area of the shape. The spacing of the adjacent transducer elements 20 is said to be "about" one wavelength to account for manufacturing tolerances, changes in transmit or receive frequency within the transducer bandwidth, and other design choices. For example, the spacing may be one wavelength of a 5 MHz second harmonic frequency within the bandwidth of a steered array, yet a 4 MHz second harmonic may be used for imaging. As another example, the spacing is two to four wavelengths at frequencies near but not at the second harmonic frequency of the fundamental transmit frequency (e.g., transmitting at a 1.75 MHz fundamental frequency using a non-steered array with a spacing based on a 3.0 or 3.6 MHz second harmonic frequency).

Figure 4A:
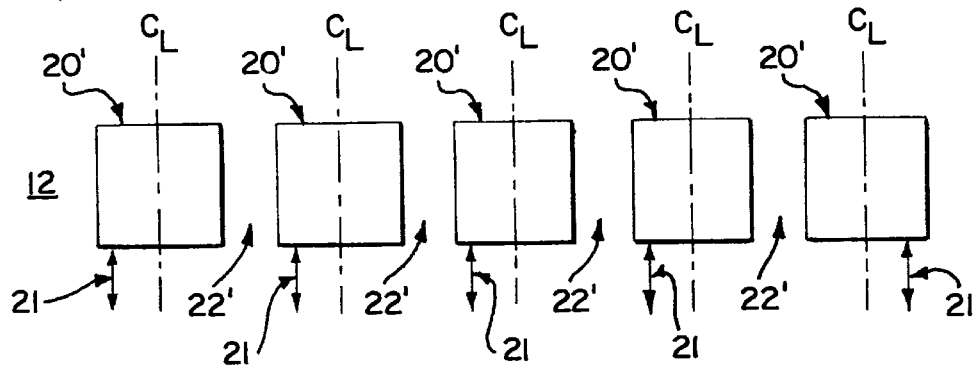
FIGS. 4A through 4C are graphical representations of various transducer element configurations.
Figure 4B:
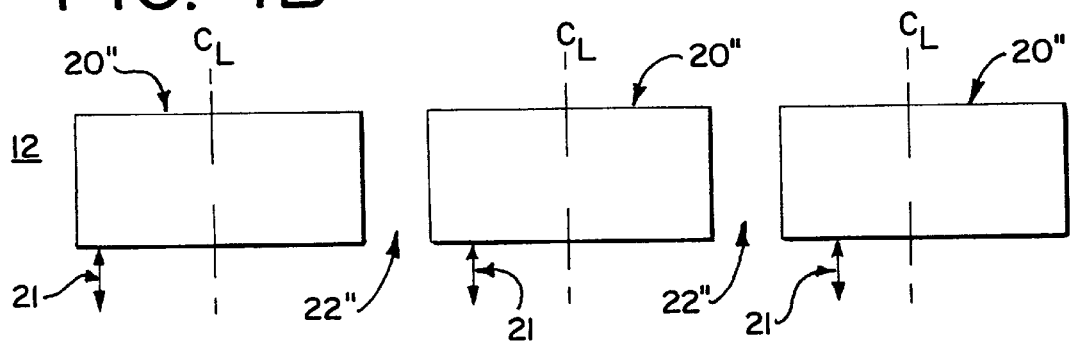
Figure 4C:
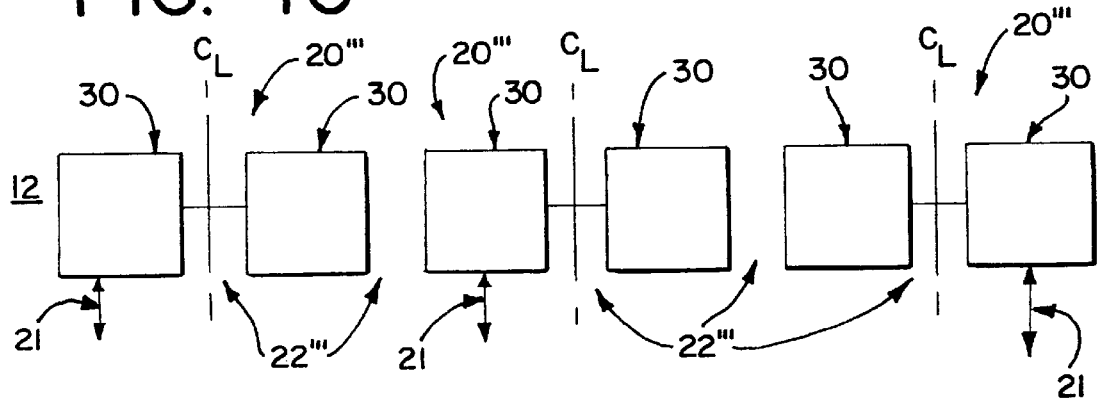

Referring to FIGS. 4A through 4C, various representations of transducer spacing are shown. In FIG. 4A, generally square transducer elements 20' are spaced about one to two wavelengths of the second harmonic of the fundamental transmit frequency from the center line of each element to the center line of any adjacent element for a steered array for imaging at the second harmonic (two to four for non-steered arrays). Each transducer element 20' is electrically addressed by a trace 21 and is separated from another transducer element 20' by the gap 22'. The gap 22' may comprise composite material or other non-conductive material. Each of the transducer elements 20' are separately electrically addressable by the trace 21 for transmitting waveforms, defining the array. The gap 22' may be of any dimension and is preferably about 0.25 to 0.30 um (e.g., such as associated with dicing). Other widths may be used, such as 40 um. In FIG. 4B, the transducer elements 20" have a spacing of about one wavelength of the second harmonic of the fundamental transmit frequency from the center line of each transducer element 20" to the center line of an adjacent transducer element 20" for a steered array. The transducer elements 20" are generally rectangular shaped (as opposed to the square shape in FIG. 4A). The gap 22" separates each transducer element 20". Transducer elements 20 with shapes that vary as a function of azimuthal position within the transducer array 12 may be used. Other shapes of transducer elements 20 may be used. Gaps 22 with different widths or varying dimensions may be used.

Referring to FIG. 4C, one embodiment of the sparse ultrasonic array 12 is shown. For example, a steered array with an element spacing that is ½ a wavelength of the highest operating frequency is converted into the sparse transducer array 12. A plurality of transducer elements 20''' are azimuthally aligned and separated by gaps 22'''. One trace 21 connects to each transducer element 22''', such as the doublet of sub-elements 30. Each transducer element 20''' comprises two or more separate transducer sub-elements 30. For example, the separate transducer sub-elements 30 are associated with a spacing of ½ a wavelength of the second harmonic of the fundamental transmit frequency and are separated by the gaps 22'''. Adjacent pairs of the transducer sub-elements 30 are shorted together by an electrical connection, such as connecting a wire between the subelements 30. The shorted together pairs of transducer sub-elements 30 comprise the respective transducer elements 20'''. The center line associated with the transducer elements 20''' is in the gap 22''' between the two shorted transducer sub-elements 30. Each transducer element 20''' is spaced from each adjacent transducer element 20''' from center line to center line by one wavelength of the highest operating frequency, such as a second harmonic of the fundamental transmit frequency. The gap 22''' between the transducer elements 20''' is one of various dimensions, but preferably a same dimension as between the two shorted sub-elements 30. In alternative embodiments, the gap 22''' between the shorted sub-elements 30 is larger or smaller than the space between the adjacent transducer elements 20'''.

The beamformer 14 generates a plurality of transmit waveforms, one for each of a plurality of the transducer elements 20 (i.e., transmit channels). Preferably, Gaussian modulated sinusoidal transmit waveforms are generated. The plurality of transducer elements 20 may comprise all or a subset of the total number of transducer elements 20. Based on various delays, the acoustic energy transmitted in response to the transmit waveforms is focused along one or more ultrasound scan lines. Additional acoustic energy is sequentially transmitted along other scan lines to generate information associated with a scanned region. The acoustic energy is transmitted along the various scan lines in a linear, Vector®, sector, curved linear or other image format.

Figure 2:
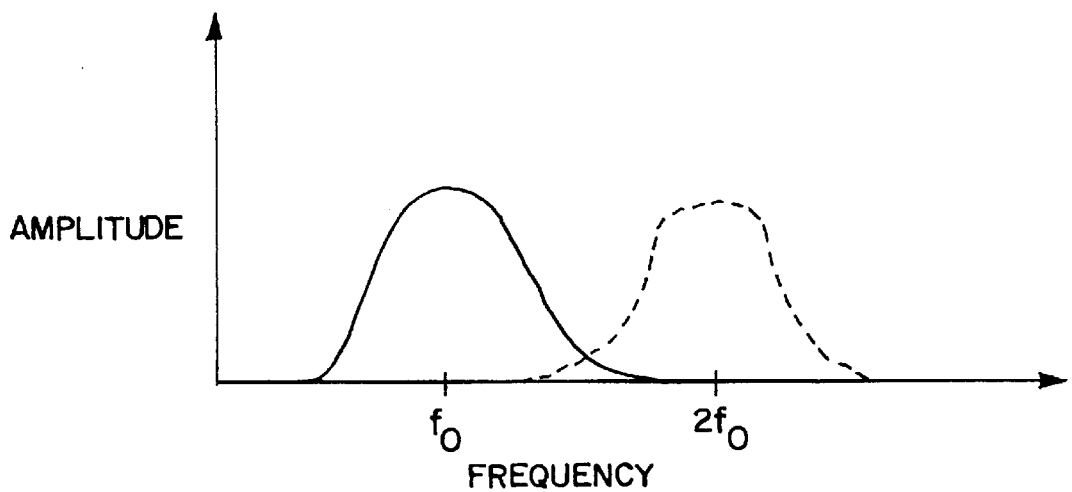
FIG. 2 is a graphical representation of frequency spectra demonstrating a fundamental frequency band and an associated second harmonic frequency band.

Using the same or a different plurality of transducer elements 20, reflected acoustic energy is converted to received signals. The beamformer 14 coherently sums the received signals and filters the signals to isolate information at a harmonic frequency of the fundamental transmit frequency. Referring to FIG. 2, the frequency spectra representing the transmit spectrum (the solid line) and the second harmonic spectrum (the dashed line) are shown. The two spectra may overlap. As used herein, the fundamental frequency includes a band of frequencies centered on the fundamental frequency, and the harmonic frequency includes a band of frequencies centered on the harmonic frequency.

The image processor 16 generates scan converted ultrasound data for the display 18 from the coherent harmonic data. The coherent data from the beamformer 14 may be processed pursuant to any of various modes, such as B-mode, Doppler flow, Doppler tissue, or combinations thereof. As used herein, ultrasound data includes data from any of the various stages of processing, such as the received signals output from the transducer 12, coherently summed data output by the beamformer 14, or data associated with various stages of processing within the image processor 16 (e.g., prior to or after scan conversion).

Using the array with a spacing of about one or two wavelengths or more of the highest operating frequency (steered and non-steered arrays, respectively) and information received at a harmonic of the fundamental transmit frequency for imaging, an image with minimized artifacts from grating lobes may be generated. Given the same number of transmit channels or transducer elements 20, a narrower beam is obtained. For example, FIG. 5A demonstrates (1) transmitting at 5 MHz (2) from a transducer with ½ wavelength of the fundamental receive frequency spacing between adjacent elements 20 and (3) receiving and filtering to obtain data at the 5 MHz fundamental frequency. The beam widths of the resulting signal are shown in FIG. 5A (e.g., −6.8 dB beam width equal to 7.91 degrees). Referring to FIG. 5B, a beam plot associated with (1) transmitting at 2.5 MHz (2) from transducer elements with a one wavelength of the 5 MHz second harmonic of the 2.5 MHz fundamental frequency spacing and (3) receiving and filtering to obtain data at the 5 MHz second harmonic frequency is shown. The beam width is more narrow (e.g., −6.8 dB beam width equal to 4.94 degrees). The narrower beam width may provide an image with greater azimuthal resolution. The increased amplitude signals shown at minus 40 to minus 20 degrees corresponds to a grating lobe suppressed by use of harmonic information.

As an alternative to using the same number of transmit channels and associated transducer elements 20, the number of transducer elements 20 and/or the associated number of traces connecting the elements to the beamformer 14 may be reduced while maintaining the overal azimuthal length of the array. For example, the sparse transducer array 12 is designed for the limited size constraints of a catheter. To obtain comparable azimuthal resolution to a transducer associated with a one-half wavelength of the receive frequency spacing, one-half the number of elements 20 and associated traces are used with a one wavelength of the highest operating frequency spacing and harmonic receive processing. For example, the catheter-based transducer described in U.S. Pat. No. 5,846,205 (U.S. application Ser. No. 08/791,598, filed Jan. 31, 1997), assigned to Acuson Corporation, the disclosure of which is incorporated herein by reference, is used. Where the transducer elements 20 are spaced with a one-half wavelength of the highest operating frequency, adjacent pairs of elements 20 are electrically connected to create half the number of transducer elements where one transducer element comprises two sub-elements 20 electrically shorted together. The spacing between adjacent elements 20 is one wavelength of the highest operating frequency. In alternative embodiments, the transducer array 12 is designed with elements 20 corresponding to a spacing of one wavelength of the highest operating frequency without shorting adjacent elements 20. In either embodiment, one-half the number of transducer elements are needed for generating a comparable azimuthal resolution to a conventional array. Preferably, the width of the transducer array is maintained, but the size requirements from the number of traces is reduced.

Space within the catheter is saved by requiring fewer transmit channels and the associated hardware, such as traces and flexible circuits. In one embodiment, the flexible circuits described in U.S. Pat. No. 5,795,299 and the traces described in U.S. Pat. No. 5,797,848, both assigned the assignee of the present invention, can be used with the catheter transducer. With less spatial demands, the transducer may be used on a catheter small enough for left ventricle imaging through insertion into the left ventricle.

Images from outside the heart are susceptible to image degradation, such as from non-uniform alignment of the muscle fibers relative to the transducer, from non-uniform wall thickness relative to the transducer, or from intervening structures. Imaging from within the left ventricle may reduce the amount of this image degradation. Images generated from within the heart or left ventricle provide more detail due to a better signal-to-noise ratio than from images generated from outside the heart or left ventricle. Imaging from within the heart, such as the left ventricle, may provide more complete images of the muscle fibers.

The harmonic imaging technique described above can be used for both tissue and contrast agent harmonic imaging. In tissue harmonic imaging, no additional non-linear contrast agent is added to the target, and only the nonlinear characteristics of the tissue are relied on to create the ultrasonic image. Medical ultrasound imaging is typically conducted in a discrete imaging session for a given subject at a given time. For example, an imaging session can be limited to an ultrasound patient examination of a specific tissue of interest over a period of ¼ to 1 hour, though other durations are possible. In this case, no nonlinear contrast agent is introduced into the tissue at any time during the imaging session.

It has been observed that tissue harmonic images provide a particularly high spatial resolution and often possess improved contrast resolution characteristics. In particular, there is often less clutter in the near field.

In contrast agent harmonic imaging, any one of a number of well known nonlinear ultrasound contrast agents, such as micro-spheres or the FS069 agent by Schering of Germany, is added to the target or subject in order to enhance the non-linear response of the tissue or fluid. The contrast agents radiate ultrasonic energy at harmonics of an insonifying energy at fundamental frequencies.

In one embodiment, the transducer array 12 is used for both harmonic and fundamental based imaging. For example, Color Doppler (i.e. Doppler flow and Doppler tissue imaging) and spectral Doppler displays operated at low frequency ranges within the transducer bandwidth and filtered to obtain fundamental information may be used. Due to the low frequency range typically used in these modes, the effect of grating lobes is minimized.

While the invention has been described above by reference to various embodiments, it will be understood that many changes and modifications can be made without departing from the scope of the invention. For example, a transducer with spacing that varies as a function of azimuthal position may be used. Harmonic information at other harmonics than the second harmonic may be used.

It is therefore intended that the foregoing detailed description be understood as an illustration of the presently preferred embodiments of the invention, and not as a definition of the invention. It is only the following claims, including all equivalents, that are intended to define the scope of the invention.

What is claimed is:

1. A method for obtaining ultrasound data with a steered array of transducer elements and an ultrasound system, the method comprising the steps of:
   (a) generating acoustic energy at a fundamental frequency from within a vessel;
   (b) receiving reflected acoustic energy responsive to the generated acoustic energy with at least a majority of adjacent transducer elements being spaced by at least about one wavelength of a highest operating frequency in the steered array; and
   (c) obtaining harmonic information from the reflected acoustic energy.

2. The method of claim 1 wherein step (b) comprises receiving the reflected acoustic energy with the array comprising every transducer element spaced by the at least the about one wavelength of the highest operating frequency from each adjacent element.

3. The method of claim 1 wherein step (b) comprises receiving the reflected acoustic energy with the array comprising a one-dimensional array selected from the group consisting of: a steered linear array, a steered curved array, a vector array, a sector array, and a curved-vector array.

4. The method of claim 1 wherein step (b) comprises receiving the reflected acoustic energy with the array selected from the group consisting of: a 1.5 dimensional steered array and a two-dimensional steered array.

5. The method of claim 1 wherein step (b) comprises receiving the reflected acoustic energy with the array comprising a catheter array.

6. The method of claim 1 wherein at least one of the majority of adjacent transducer elements comprises at least two sub-elements shorted together and connected to a single electrical trace.

7. The method of claim 1 wherein step (b) comprises receiving the reflected acoustic energy comprising an azimuthal beam width that is more narrow than an azimuthal beam width associated with generating the acoustic energy with a transducer elements spacing of about one half the wavelength of the highest operating frequency and the same number of transducer elements.

8. The method of claim 1 wherein step (b) comprises receiving the reflected acoustic energy comprising a lateral resolution that is similar to a lateral resolution associated with generating the acoustic energy with a transducer element spacing of about one half the wavelength of the highest operating frequency and about twice a number of transducer elements.

9. The method of claim 1 wherein step (c) comprises filtering the reflected energy.

10. The method of claim 1 wherein the at least the majority of adjacent transducer elements are spaced by the at least about one wavelength of the highest operating frequency from a center of a first of the majority of adjacent transducer elements to a center of a second of the majority of adjacent transducer elements, the first transducer element is adjacent the second transducer element.

11. The method of claim 1 wherein the at least the majority of adjacent transducer elements are spaced by about 1.5 the wavelength of the highest operating frequency.

12. The method of claim 1 wherein the highest operating frequency and the harmonic frequency comprise a second harmonic of the fundamental frequency.

13. A method for obtaining ultrasound data with a non-steered array of transducer elements and an ultrasound system, the method comprising the steps of:
   (a) generating acoustic energy at a fundamental frequency
   (b) receiving reflected acoustic energy from the non-steered array, the non-steered array comprising a majority of adjacent elements spaced at least about two wavelengths of a highest operating frequency; and
   (c) obtaining information at a harmonic of the fundamental transmit frequency from the reflected acoustic energy.

14. The method of claim 13 wherein the elements are spaced by the at least about two wavelengths from a center of each element to a center of another element.

15. The method of claim 13 wherein step (c) compensates at least in part for grating lobes generated by the spaced adjacent elements.

16. The method of claim 13 wherein step (b) comprises receiving the reflected acoustic energy with the non-steered array comprising a catheter array.

17. The method of claim 13 wherein at least one of the elements comprises at least two sub-elements shorted together and connected to a single electrical trace.

18. The method of claim 13 wherein step (b) comprises receiving the reflected acoustic energy comprising an azimuthal beam width that is more narrow than an azimuthal beam width associated with generating the acoustic energy with a transducer element spacing of about one wavelength of the highest operating frequency and the same number of transducer elements.

19. The method of claim 13 wherein step (b) comprises receiving the reflected acoustic energy comprising a lateral resolution that is similar to a lateral resolution associated with generating the acoustic energy with a transducer elements spacing of about one wavelength of the highest operating frequency and about twice a number of transducer elements.

20. The method of claim 13 wherein step (c) comprises filtering the reflected acoustic energy.

21. The method of claim 13 wherein the adjacent elements are spaced at least about 3 wavelengths of the highest operating frequency.

22. The method of claim 13 wherein the highest operating frequency and the harmonic frequency comprise a second harmonic of the fundamental frequency.

23. An ultrasound system for obtaining ultrasound data with a steered array of transducer elements, the ultrasound system comprising:
   the steered array of transducer elements on a catheter, the steered array having at least a majority of adjacent transducer elements that are spaced by at least about one wavelength of a highest operating frequency; and
   a beamformer operatively connected to the steered array for obtaining information at a harmonic of a fundamental transmit frequency.

24. The system of claim 23 wherein every one of the transducer elements of the steered array are spaced by at least the about one wavelength of the highest operating frequency from each adjacent element.

25. The system of claim 23 wherein the steered array comprises a one-dimensional array selected from the group consisting of: a steered linear array, a steered curved array, a Vector® array, a sector array, and a curved-vector array.

26. The system of claim 23 wherein the steered array comprises an array selected from the group consisting of: a 1.5 dimensional steered array and a two-dimensional steered array.

27. The system of claim 23 wherein at least one of the two adjacent transducer elements comprises at least two sub-elements shorted together and connected to a single electrical trace.

28. The system of claim 23 wherein the steered array is operable to receive acoustic energy comprising an azimuthal beam width that is more narrow than an azimuthal beam width associated with generating the acoustic energy with a transducer element spacing of about one half the wavelength of the highest operating frequency.

29. The system of claim 23 wherein the steered array is operable to receive acoustic energy comprising a lateral resolution that is similar to a lateral resolution associated with transmitting the acoustic energy with a transducer element spacing of about one half the wavelength of the highest operating frequency with twice a number of transducer elements.

30. The system of claim 23 wherein the beamformer comprises a filter operable to substantially isolate the information at the harmonic frequency.

31. The system of claim 23 wherein the at least the majority of adjacent transducer elements are spaced by the at least about one wavelength of the highest operating frequency from a center of a first of the two adjacent transducer elements to a center of a second of the two adjacent transducer elements.

32. The system of claim 23 wherein the at least about one wavelength comprises at least about 1.5 wavelengths.

33. The system of claim 23 wherein the operating frequency and the harmonic frequency comprise a second harmonic of the fundamental transmit frequency.

34. An ultrasound system for obtaining ultrasound data with a non-steered array of transducer elements, the ultrasound system comprising:
   the non-steered array of transducer elements having at least a majority of adjacent transducer elements that are spaced by at least about two wavelengths of a highest operating frequency; and
   a beamformer operatively connected to the non-steered array for obtaining information at a harmonic of a fundamental transmit frequency.

35. The system of claim 34 wherein every one of the transducer elements of the non-steered array are spaced by at least the about two wavelengths from each adjacent element.

36. The system of claim 34 the non-steered array comprises a one-dimensional array selected from the group consisting of: a linear array and a curved array.

37. The system of claim 34 wherein the non-steered array comprises an array selected from the group consisting of: a 1.5 dimensional array and a two-dimensional array.

38. The system of claim 34 wherein the non-steered array comprises a catheter array.

39. The system of claim 34 wherein at least one of the majority of adjacent transducer elements comprises at least two sub-elements shorted together and connected to a single electrical trace.

40. The system of claim 34 wherein the non-steered array is operable to transmit acoustic energy comprising an azimuthal beam width that is more narrow than an azimuthal beam width associated with generating the acoustic energy with a transducer element spacing of about one wavelength of the highest operating frequency and a similar number of transducer elements.

41. The system of claim 34 wherein the array is operable to transmit the acoustic energy comprising a lateral resolution that is similar to a lateral resolution associated with transmitting the acoustic energy with a transducer element spacing of about one wavelength of the highest operating frequency and about twice a number of transducer elements.

42. The system of claim 34 wherein the beamformer comprises a filter operable to substantially isolate the information at the harmonic frequency.

43. The system of claim 34 wherein the at least the majority of adjacent transducer elements are spaced by the at least about two wavelengths of the highest operating frequency from a center of a first of the two adjacent transducer elements to a center of a second of the two adjacent transducer elements.

44. The system of claim 34 wherein the at least about two wavelengths comprises at least about 3 wavelengths.

45. The system of claim 34 wherein the operating frequency and the harmonic frequency comprise a second harmonic of the fundamental transmit frequency.

* * * * *